(12) United States Patent
Mielekamp et al.

(10) Patent No.: US 11,026,648 B2
(45) Date of Patent: Jun. 8, 2021

(54) VOLUME PRESENTATION FOR PLANNING A LOCATION OF AN INJECTION POINT

(71) Applicant: KONINKLIJKE PHILIPS N.V., Eindhoven (NL)

(72) Inventors: Pieter Maria Mielekamp, Veldhoven (NL); William Edward Peter Van Der Sterren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/335,428

(22) PCT Filed: Sep. 22, 2017

(86) PCT No.: PCT/EP2017/073973
§ 371 (c)(1),
(2) Date: Mar. 21, 2019

(87) PCT Pub. No.: WO2018/055068
PCT Pub. Date: Mar. 29, 2018

(65) Prior Publication Data
US 2020/0015768 A1 Jan. 16, 2020

(30) Foreign Application Priority Data

Sep. 23, 2016 (EP) .................................... 16190262

(51) Int. Cl.
*A61B 6/00* (2006.01)
*A61B 34/10* (2016.01)
(Continued)

(52) U.S. Cl.
CPC .............. *A61B 6/507* (2013.01); *A61B 6/032* (2013.01); *A61B 6/469* (2013.01); *A61B 6/504* (2013.01);
(Continued)

(58) Field of Classification Search
CPC . G06T 2207/30056; G06T 2207/30096; G06T 2207/30104; G06T 2210/36;
(Continued)

(56) References Cited

U.S. PATENT DOCUMENTS

| 5,802,133 A | 9/1998 | Kawai |
| 8,630,470 B2 | 1/2014 | Pichon |

(Continued)

FOREIGN PATENT DOCUMENTS

| JP | H0647022 A | * | 2/1994 |
| JP | 2003109030 A | | 4/2003 |

(Continued)

OTHER PUBLICATIONS

Lin, Mingde et al "Evaluating Tumors in Transcatheter Aterial Chemoembolization (TACE) using Dual-Phase Cone-Beam CT", Minimally Invasive Therapy & Allied Technology, vol. 20, No. 5, Sep. 2011, pp. 276-281.

(Continued)

*Primary Examiner* — Amandeep Saini

(57) ABSTRACT

Visualization of a region of interest and planning a location of at least one injection point for a medical procedure is provided. At least one volume of imaging data for a region of interest is received. At least one virtual injection point is obtained. The at least one injection point indicates a location in a network of blood vessels for at least one injection. First and second rendering modules are controlled to construct a combined volume presentation including a first volume region rendered by a first rendering module at a relatively low level of detail and a second volume region is rendered at a higher level of detail by a second rendering module. The first and second volume regions are designated based on the at least one virtual injection point.

15 Claims, 6 Drawing Sheets

(51) Int. Cl.
*A61B 6/03* (2006.01)
*G06T 15/08* (2011.01)

(52) U.S. Cl.
CPC .............. *A61B 34/10* (2016.02); *G06T 15/08* (2013.01); *A61B 6/4085* (2013.01); *A61B 6/4441* (2013.01); *A61B 6/481* (2013.01); *A61B 2034/107* (2016.02); *G06T 2207/30056* (2013.01); *G06T 2207/30096* (2013.01); *G06T 2207/30104* (2013.01); *G06T 2210/36* (2013.01); *G06T 2210/41* (2013.01)

(58) Field of Classification Search
CPC ....... G06T 2210/41; G06T 2207/30101; A61B 6/507; A61B 34/10; A61B 6/032; A61B 6/469; A61B 6/504; A61B 15/08; A61B 2034/107; A61B 6/4085; A61B 6/4441; A61B 6/481
USPC ......................................................... 382/131
See application file for complete search history.

(56) References Cited

U.S. PATENT DOCUMENTS

2006/0052690 A1* 3/2006 Sirohey ................. A61B 8/481
600/420
2011/0002517 A1* 1/2011 Mollus ................... G06F 19/00
382/130
2012/0283556 A1 11/2012 Ferschel
2015/0178467 A1 6/2015 Britzen
2015/0242588 A1* 8/2015 Audigier .............. A61B 6/5217
606/41

FOREIGN PATENT DOCUMENTS

| JP | 2013222361 A | * | 10/2013 | ............. G06T 19/00 |
| WO | WO-2006085288 A2 | * | 8/2006 | ................ G06T 7/70 |
| WO | 2006085288 A2 | | 9/2006 | |
| WO | 2009109887 A1 | | 9/2009 | |
| WO | 2016055899 A1 | | 4/2016 | |

OTHER PUBLICATIONS

Minami, Yasunori et al "Tracking Navigation Imaging of Transcatheter Arterial Chemoembolization for Hepatocellular Carcinoma using Three-Dimensional Cone-Beam CT Angiography", Liver Cancer, vol. 3, 2014, pp. 53-61.

Pichon, Eric et al "Development and preliminary evaluation of software for planning selective liver embolizations from three dimensional fluoroscopy imaging", Int J Cars (2008) vol. 3, pp. 405-412.

* cited by examiner

1

VOLUME PRESENTATION FOR PLANNING A LOCATION OF AN INJECTION POINT

CROSS-REFERENCE TO PRIOR APPLICATIONS

This application is the U.S. National Phase application under 35 U.S.C. § 371 of International Application No. PCT/EP2017/073973, filed on Sep. 22, 2017, which claims the benefit of European Patent Application No. 16190262.2, filed on Sep. 23, 2016. These applications are hereby incorporated by reference herein.

FIELD OF THE INVENTION

The technical field generally relates to visualization of a region of interest by way of a volume presentation and planning a location of an injection point. In particular, the volume presentation allows planning of an injection point for a transarterial catheter embolization procedure.

BACKGROUND OF THE INVENTION

A technique called transarterial catheter embolization (TACE) is used to deliver cancer treatment directly to a tumor through minimally-invasive means. A combination of chemotherapy drugs and embolization material is used to block off (embolize) the blood supply to the tumor.

The TA(C)E procedure is typically performed in the "angio-suit". By puncturing the common femora artery in the right groin or the radial artery in the wrist, a catheter is guided through the arterial system near the area to be treated.

Here, a micro catheter is guided in the proper distal artery that supplies the tumor, where the agent is pushed into the tumor. This (super) selective embolization is done to maximize the amount of chemotherapeutic/embolic agent that is directed to the tumor and to minimize the amount of the therapeutic material that could damage the normal tissue.

Important aspects to the success of the TA(C)E routine are the detection of all the tumors, full coverage of the detected tumors with the therapeutic drug, embolization of all the feeding arteries, optimized selectivity to limit damage the normal tissue, particularly liver tissue. It is desirable to optimize the injection(s) for full feeder embolization and lesion coverage, with optimal selectivity.

The optimal visualization of tumor feeding blood vessels and parenchymal space are important to determine catheter position and injection parameters for (chemo) embolization drug delivery, and can ultimately impact the treatment outcomes.

The development of C-arm cone-beam computed tomography (CBCT) has greatly aided in the detection and visualization of tumors. The introduction of dual phase cone beam CT has led to an increase in detection of liver tumors.

A description of the use of dual phase CBCT is provided in "Evaluating tumors in transcatheter arterial chemoembolization (TACE) using dual-phase cone-beam CT", Minimally Invasive Therapy & Allied Technol. 2011 September; 20(5): 276-281, doi: 10.3109/13645706.2010.536243. Here, C-arm cone-beam computed tomography (CBCT) is used to visualize tumor-feeding vessels and parenchymal staining during transcatheter arterial chemoembolization (TACE). A feasibility study is presented of software that allows a CBCT system to capture the two phases using only one contrast injection. The software enables acquisition of two sequential, back-to-back, CBCT scans (dual-phase CBCT, DPCBCT) so both tumor feeding vessels and parenchyma are captured using only one contrast injection. Image acquisition can occur with both clockwise and counter-clockwise C-arm rotations, image reconstruction of both scans occurs after the completion of both scans, and both reconstructed datasets are displayed side-by-side. By displaying the scans side by side, the software allows for simultaneous cine viewing. The software disclosed is considered to allow improved information about the number and distribution of tumors.

Following vessels in slice presentations can be cumbersome because of their discontinuity, which necessitates mental interpretation while browsing through the slices. A 3D volume presentation would be advantageous since the whole vessel tree branching structure is presented in one view. However, a highly detailed volume presentation provides an overload of visual information and can be processing intensive, whilst a lower detail presentation may not be able to visualize all lesions/feeders. Yet, the smallest detail may influence the treatment to avoid future recurrences.

Thus, it is desired to provide a visualization technique that allows structures, such as lesions and feeders, in a region of interest to be identified with increased accuracy in a processing efficient way to allow for practical implementation. It is further desirable to provide a visualization technique that allows for enhanced planning of where to position an injection point to optimally treat a lesion.

WO 2009/109887 A1 discloses a method of image processing of images of a tube system. A tube model is gathered from a specific tube data set. A user may select a virtual injection point of a medium, define a direction with respect to the virtual injection point, and simulate a dynamic flow of the medium starting at the virtual injection point. At least two dynamic images are generated and displayed, so as to provide a three dimensional visualization of a simulated medium flow.

SUMMARY OF THE INVENTION

Hence, there may be a need to provide an improved and facilitated way of visualizing imaging data for planning at least one location of an injection point.

Generally, embodiments of the present invention relate to a combined volume presentation mode where, based on at least one indicated injection point, distal end features, behind the injection points, will be enhanced by means of a dedicated, high detail, injected volume rendering implementation. An injection simulation can be run based on an injection from the at least one indicated injection point. An injection volume representing a volume of tissue reached by the injection can be determined based on the injection simulation. The combined volume presentation visualizes the injection volume using the high detail volume rendering implementation.

The object of the present invention is solved by the subject-matter of the independent claims; wherein further embodiments are incorporated in the dependent claims. It should be noted that the following described aspects of the invention apply also for the image processing system, for the imaging system, for the medical system and for the computer implemented method as well as for the computer program element and the computer readable medium.

Methods, image processing systems, systems and computer programs are provided for visualization of a region of interest and planning a location of at least one injection point for a medical procedure. In particular, at least one volume of imaging data for a region of interest is received. At least one virtual injection point is obtained. The at least one injection point indicates a location in a network of blood vessels for at least one injection. First and second rendering modules are controlled to construct a combined volume presentation including a first volume region rendered by a first rendering module at a relatively low level of detail and a second volume region is rendered at a higher level of detail by a second rendering module. The first and second volume regions are designated based on the at least one virtual injection point.

Such a combined volume presentation allows a more detailed volume of the region of interest to be displayed for a relevant region relative to at least one virtual injection point and a lower detailed volume for other regions to be displayed so that a processing efficient and user intuitive presentation can be provided that allows accurate identification of structures, such as lesions and feeders, in a relevant region relative to the at least one virtual injection point.

In an embodiment, a user selection of the at least one virtual injection point is received. Accordingly, a user is able to interactively try out different injection points through a user interface module to control visualization of features relative to the virtual injection point. The user input may be through a selection of a point in a volume presentation.

The second volume region is located in the combined volume presentation downstream of the at least one virtual injection point relative to a direction of blood flow in the network of blood vessels. Accordingly, an injection area relative to a virtual injection point is viewed in a detail enhanced way.

In an embodiment, the imaging data dual phase computed tomography imaging data including arterial phase imaging data and delayed phase imaging data. The first rendering module renders the arterial phase imaging data and the second rendering module renders registered arterial phase imaging data and delayed phase imaging data. The arterial phase imaging data is enhanced by the delayed phase imaging data and is able to show distal features relative to an injection point more clearly than in a single phase embodiment.

The first and second rendering modules may alternatively operate on the same volume of imaging data, yet render the imaging data at different levels of detail. This embodiment allows registration and dual phase enhancement processing to be avoided to reduce processing requirements as compared to the dual phase embodiment.

At least one adapted virtual injection point may be obtained based on a received command to add at least one virtual injection point, delete at least one virtual injection point, or to move at least one virtual injection point. The first and second rendering modules are controlled to construct an adapted combined volume presentation including first and second volume regions, respectively rendered by the first and second rendering modules, designated based on the at least one adapted virtual injection point. Accordingly, the combined volume presentation can be iteratively adapted by changing at least one virtual injection point. The combined presentation is able to show in high detail an injection area downstream of the at least one virtual injection point and the injection area will adapt depending upon selection of virtual injection points. This provides a powerful planning tool. The at least one adapted virtual injection point may be user selected.

In an embodiment, an injection simulation module simulates an injected region from each at least one virtual injection point. The first and second volume regions of the combined presentation are designated based on the injected region. In particular, the simulation module is able to produce a volume map labelling voxels of the imaging data as being reached by an injection from each at least one virtual injection point based on an injection simulation so as to derive the injected region. The area rendered by the first rendering module and the area rendered by the second rendering module can be designated based on the volume map. An injection simulation based solution provides a processing efficient, yet effective way to show an injected region in the combined volume presentation and thus appropriately demarcate the high and low detail areas of the combined volume presentation.

In an embodiment, the injected region is simulated from each at least one virtual injection point by processing the at least one volume of imaging data using a virtual perfusion algorithm that estimates injection material perfusion from each at least one virtual injection point. An exemplary virtual perfusion algorithm is based on computation of a geodesic potential distance map that encodes a probability distance that any location in the data is from a reference point following blood vessels. The probability distance is determined based on arc length distance and a potential term that mathematically favors paths that follow more intense imaging data (i.e. blood vessel in imaging data obtained from contrast enhanced imaging). Such a geodesic potential distance map allows the injected region to be simulated without processor intensive segmentation of the imaging data.

In an embodiment, the combined volume presentation is constructed to include a highlighted volume region that has been graphically highlighted to indicate tissue reached by an injection from each at least one virtual injection point. The highlighted volume region may be based on the simulation. This feature of the present disclosure allows fast checking of the perfusion result of a candidate injection.

The following features provide further visualization options that can improve assessment and/or determination of injection points for a medical procedure such as an embolization procedure in a processing efficient way.

In an embodiment, an injected region is determined based on the at least one virtual injection point non-injected vessels are determined in a neighborhood region to the injected region. The first and second rendering modules may construct the combined volume presentation so that the second volume region includes the injected region and the non-injected region and/or the non-injected vessels are graphically highlighted. This provides a check for an operative that a selected virtual injection point is not missing important feeder vessels leading to a lesion in a neighbor region defined around the injected region. The neighborhood region may be determined based on a scaler enlargement of the injected region. The non-injected vessels can be found using path finding logic and the neighborhood region.

In an embodiment, a segmentation module segments a lesion from the imaging data. The lesion may be graphically highlighted in the combined volume presentation.

In an embodiment, an automatic feeder determination module determines at least one feeder vessel to a lesion. A feeder path along the at least one determined feeder vessel to the lesion is graphically highlighted. The feeder path may be determined using a path finding algorithm.

In an embodiment, an automatic injection member path determination module obtains a location of a distal end of a catheter that feeds an injection device and automatically determine an injection member path from the location of the catheter distal end to the virtual injection point through the network of blood vessels. The injection member path is graphically highlighted in the combined volume presentation. The injection member path may be determined using a path finding algorithm.

In an embodiment, a rendering selection module allows a user to select at least one visual aspect of at least one of the first and second rendering modules. In this way, the detailed area of the combined volume presentation can be visually enhanced by adjusting visual setting of the second rendering module.

In an embodiment, an automatic virtual injection point determination module automatically determines the at least one virtual injection point based on a location of a lesion obtained from the at least one volume of imaging data and a path to the lesion. The first and second volume regions are designated based on the automatically determined at least one virtual injection point. The path to the lesion may be automatically determined. Further, the path from a catheter to the automatically determined virtual injection point can be automatically determined. In this way, a user can merely select a lesion in a visualization of the imaging data and the path to the lesion and the virtual injection point can be automatically determined. Further, the dual detail rendering can be determined based on the automatically determined virtual injection point along with graphical highlights of a path from a catheter to a virtual injection point all based on a single selection. By automatically determined herein, it is meant that the features are determined through computer based data processing using suitable computer algorithms.

In various embodiments, the second rendering module renders at a higher spatial resolution than the first rendering module.

Also disclosed is a computer program element adapted to implement an image processing system as described herein or adapted to perform the method steps described herein when executed by at least one processor.

A computer readable medium having stored the computer program element.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the application and uses. Furthermore, there is no intention to be bound by any expressed or implied theory presented in the preceding technical field, background, brief summary or the following detailed description.

The following disclosure is particularly provided with reference to TACE procedures, particularly for embolization of liver tumors. However, other applications of the present visualization and injection planning methods and systems are possible.

Figure 1:
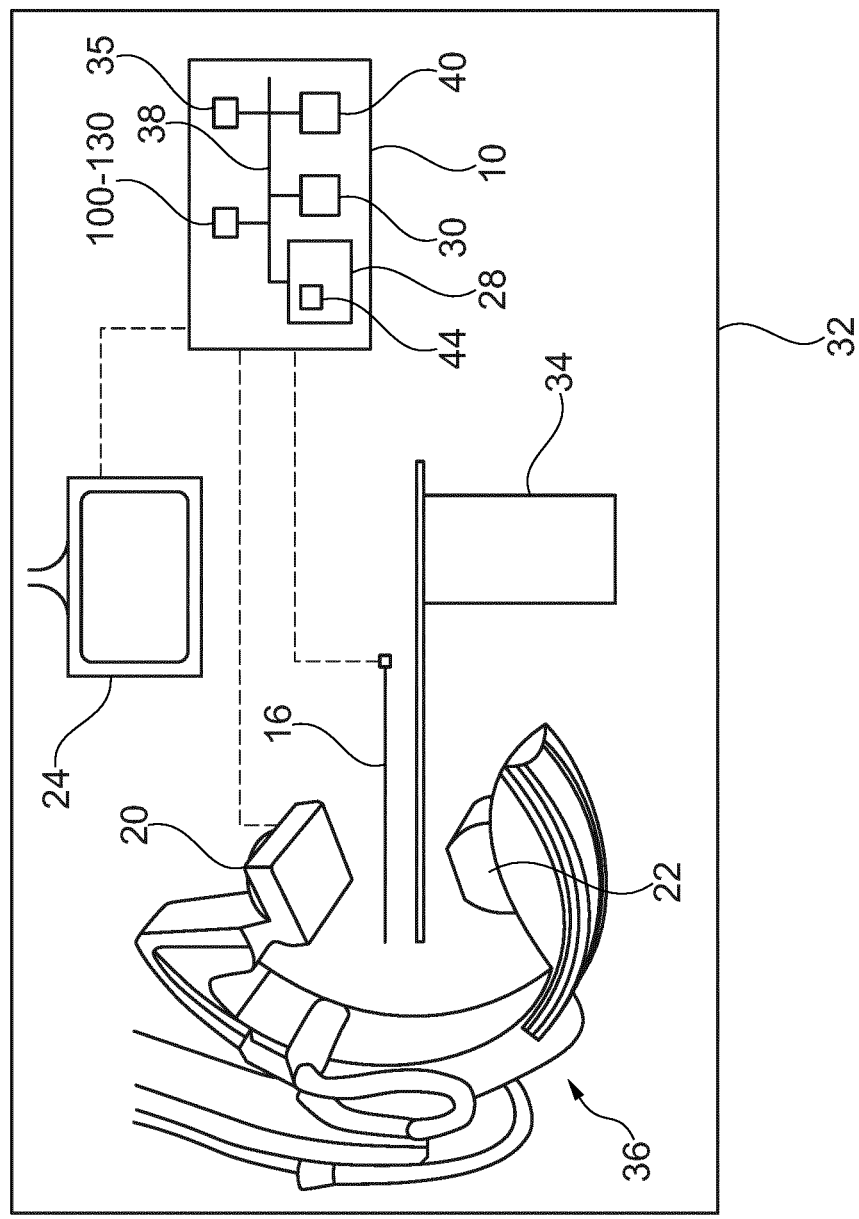
FIG. 1 is a schematic view of a medical system including a transarterial medical device, an imaging machine, a display unit and an image processing system.

FIG. 1 is a schematic view of a medical system 32 comprising an extracorporeal imaging machine 36, an image processing system 10, a display unit 24, a medical device 16 and a patient support table 34.

The imaging machine 36 is configured for generating imaging data of a patient supported on a table 34. The imaging machine 36 comprises a detector 20 and an X-ray generator 22. The imaging machine 36 is configured for X-ray imaging. The imaging machine 36 may be configured for angiographic imaging. The imaging machine 36 is configured for generating three-dimensional imaging data. In a specific embodiment, the imaging machine 36 is a computed tomography (CT) imaging machine having a C-arm configuration, with the detector 20 at one end of the C-arm and an X-ray generator 22 at the other end of the C-arm. In the specific embodiment, the imaging machine 36 is a cone beam computed tomography imaging machine (CBCT) configured for executing dual phase CT measurements to obtain dual phase CBCT imaging data.

The image processing system 10, such as a general purpose computer, is operably connected to the imaging machine 36 controls operation of the imaging machine 36 for performing scans to obtain imaging data and processes the imaging data from the imaging machine 36. The processed imaging data may be presented on the display unit 24 of the medical system 32.

The image processing system 10 comprises at least one processor 30. The processor 30 is operably connected to a memory 28. The processor 30 and the memory 28 may be connected through a bus 38. The processor 30 may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like. Moreover, the processor 30 may be embodied in a general purpose computer.

Figure 2:
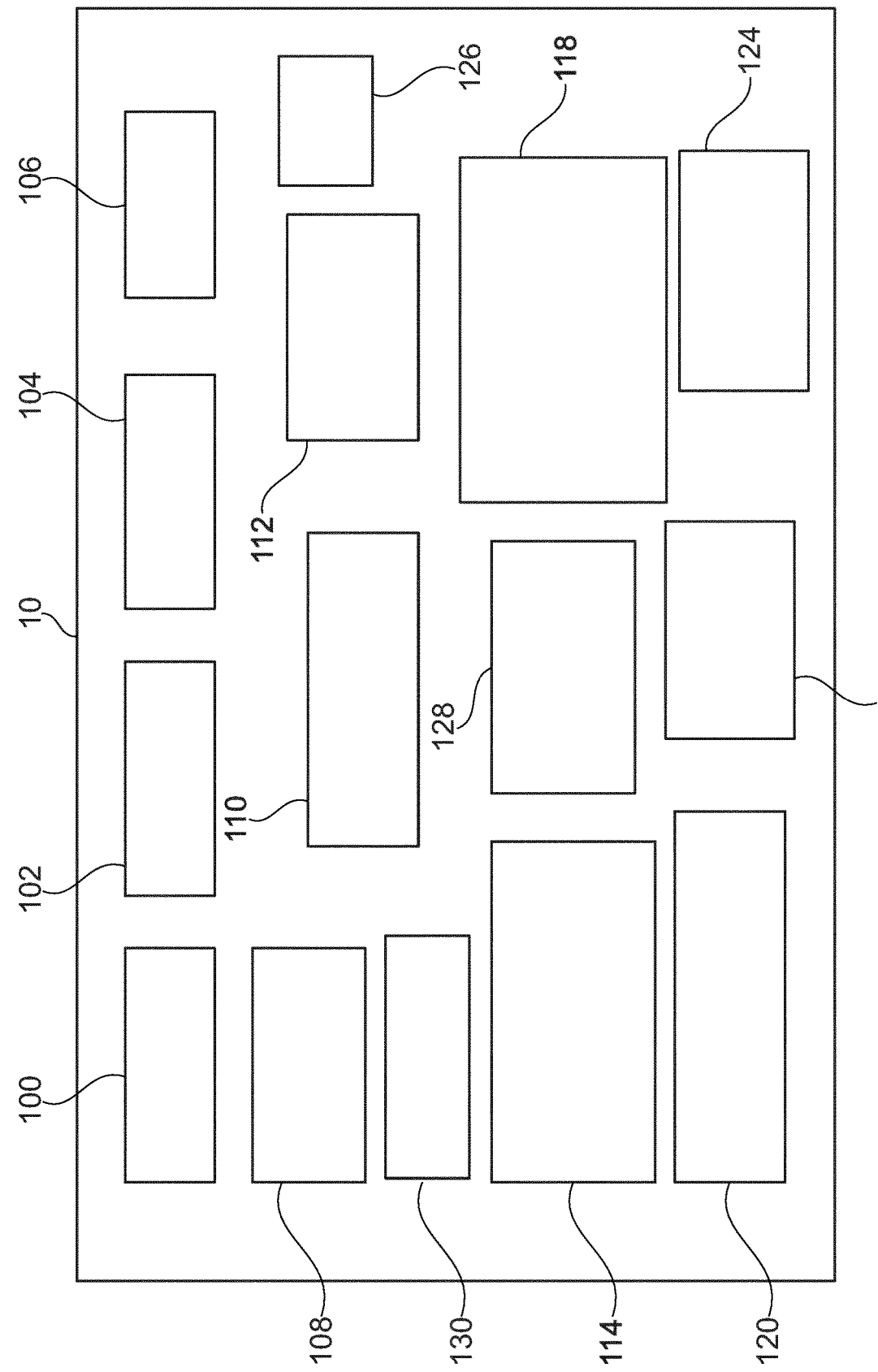
FIG. 2 is a block diagram of modules of the image processing system.

The image processing system 10 comprises a number of modules 100-130, shown in detail in FIG. 2, for executing the image processing systems and methods described herein, particularly with reference to FIGS. 3 to 6. As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality. In particular, the modules 100-130 described herein include at least one processor, a memory and computer program instructions stored on the memory for implementing the various functions and processes described with respect to the modules 100-130. Although separate modules 100-130 are described herein for particular functions, this does not exclude an integrated topology. Further, the shown modules 100-130 may be divided into further sub-modules. The modules 100-130 are in communication with one another as necessary to implement the features, processes and systems described herein.

A display generation module 40 is also operably connected to the processor 30 through the bus 38. The display generation module 40 is configured to generate, with the processor 30, display of images for the display unit 24. The display generation module 40 may be implemented by hardware, software or a combination thereof. The display generation module 40 makes use of first and second rendering modules 102, 104 and other modules (shown in FIG. 2) for displaying the combined volume presentation described herein. The display generation module 40 may be included as programming instructions for the processor 30 and stored on the memory 28. The display unit 24 may be any monitor, screen, or the like suitable for presenting a graphical user interface (GUI) capable of presenting medical images.

In the shown embodiment, the imaging machine 36 is operably connected to the processor 30. The imaging machine 36 obtains imaging data; which data is provided to the processor 30 for processing to create a three dimensional volume presentation of a region of interest of a vascular network via the display generation module 40. The three dimensional volume presentation may then be presented on the display unit 24.

The memory 28 has encoded thereon, at least one computer program 44 or computer program element 44, providing instructions which are executable by the processor 30 to process images from the imaging machine 36. In addition to the computer program 44 for processing the imaging data for presentation on the display unit 24, a computer program 44 is also provided that performs a combined three dimensional volume presentation of a region of interest as described herein, particularly with reference to the data flow diagrams of FIGS. 3 and 4 and with reference to the presentations and methods described with respect to FIGS. 5, 6 and 7.

FIG. 1 discloses a medical system 32 comprising the image processing system 10, the CBCT imaging machine 36 for obtaining CBCT imaging data, the TACE device for delivering embolization material at an injection point, a tracking system 35 for tracking a position of a reference part, usually the distal end, of the TACE device 16, and a display unit 24 for displaying a combined three dimensional volume presentation. The image processing system 10, the CBCT imaging machine 36 and the tracking system 35 can be considered as comprising in a general imaging system.

The TACE device 16 comprises a catheter (not separately shown) that is able to navigate through a vascular network from an entry point to a position adjacent a target lesion. The TACE device 16 includes an injection member that can be extended from a distal end of the catheter to an injection point and can be operated to injection embolization material. The injection member may be a micro catheter disposed within the delivery catheter. The embolization material may include blood vessel occluding agents such as beads and/or microspheres and optionally other drugs such as cancer treating drugs and chemotherapy agents. For example, the TACE device 16 can be operated to inject lipiodol, drug-eluting beads, and Yttrium-90 radioembolizing microspheres.

The tracking system 35 may comprise an image based tracking system in which the two dimensional catheter tip is automatically detected in live fluoroscopic images. By projecting the tip position on a three dimensional volume presentation, a three dimensional position of the tip can be established. Accordingly, the tracking system 35 of the present embodiment allows automatic establishment of a reference point of the TACE device 16, particularly a catheter thereof, through image analysis techniques.

According to the present disclosure, the medical system 32 is useful for assisting a TACE procedure. The TACE device 16 is positionable at a target site of a region of interest in order to inject embolization material (and optionally also other tumor treating drugs such as chemotherapy agents) for occluding flow of blood to the target lesion. In order to minimize collateral damage and maximize lesion treatment, the imaging machine 36 and the image processing system 10 are operable, through the various modules described further below, with the TACE device 16 in situ. The present imaging system allows generation of a combined volume presentation by way of first and second rendering modules 102, 104 (FIG. 2) operating two different transfer functions: a low detail transfer function to visualize the main vessel structure proximal to a candidate injection point, and a high detail transfer function to visualize small details from the injection point up to and including a tumor area. In one implementation, the low-detail visualization is based on an arterial phase volume and the high-detail visualization is based on the enhancement phase volume of dual phase imaging data obtained by the imaging machine 36. The candidate injection point can be user selected through a user interface module 108 (FIG. 2) or automatically determined through an automatic virtual injection point determination module 118 (FIG. 2). More than one virtual injection point may be selected. Virtual injection points can be added, deleted or moved and the image processing system 10 will adapt the displayed combined presentation accordingly. The two levels of detail provided by the combined presentation described herein provide processing efficient, enhanced visualization for a user of the outcome of a corresponding medicament injection for planning one or more injection points for treatment of a target lesion. Once the planning is deemed satisfactory through use of the present imaging processing system 10, the TACE device can be correspondingly operated to inject embolization material at the proposed injection points, possibly through use of imaging guidance by way of the tracking system 35.

Modules of the processing system 10, data flows executed by such modules and visualization possibilities enabled by the present disclosure will now be described in detail with reference to FIGS. 2 to 7, whilst continuing to refer to the medical system 32 of FIG. 1.

With reference to FIG. 2, the image processing system 10 includes a data receiving module 100 that is configured for receiving tomographic imaging data. The imaging data is obtained by the imaging machine 36. The tomographic imaging data may comprise first and second volumes of imaging data including respective phases of a dual phase imaging procedure. Alternatively, the image processing system 10 operates without a dual phase procedure in which case a single volume of imaging data can be received by the data receiving module 100. The imaging data includes imaging data covering a region of interest (such as including a liver or part thereof), at least one target lesion, a distal end of the TACE device 16 in situ in a vascular network and adjacent the target lesion. The imaging data is contrast enhanced so that the vascular network can be readily contrasted from other tissue. The imaging data is made up of voxels of imaging data (data points arranged in three dimensions) and each voxel comprises at least a value representing intensity of X-ray radiation attenuation, usually measured in Hounsfield units (HU).

The image processing system 10 includes first and second rendering modules 102, 104. The first and second rendering modules 102, 104 execute known image processing techniques to render a two dimensional projection from a three dimensional volume of imaging data for display by the display unit 24. Since the rendering techniques provide a projection of the three dimensional volume of imaging data, a sense of a three dimensional volume being constructed is provided on the display unit 24.

The first rendering module 102 is a lower detail renderer than the second rendering module 104. That is, the first rendering module 102 has a lower detail voxel transfer function than the second rendering module 104. In particular, the first rendering module 102 samples imaging data and renders such imaging data at a lower level of spatial resolution than the second rendering module 104. For example, the first rendering module 102 may operate at a low resolution of 384^3 and the second rendering module may operate at a higher resolution of 512^3 for the same volume of tissue. The imaging data obtained by the imaging machine 36 may be at the higher resolution of the second rendering module 104 or higher and may be sampled at a lower resolution by the first rendering module 102. Alternatively, the imaging data may be provided through some sampling module so that the imaging data is received by the data receiving module at different spatial resolutions (high and low), which are used by the different rendering modules 102, 104 to render the imaging data at different spatial resolutions.

The first and second rendering modules 102, 104 have different spatial resolutions, and may additionally have different rendering methods, contrast/brightness transfer functions, color schemes and/or white space speed optimization methods. The first and second rendering modules 102, 104 may allow for independent control, such as user control, of visual aspects of rendering settings including contrast/brightness, rendering option (Gradient, Max Intensity Projection, Volume rendering and/or pre integrated volume presentation etc.). The user may be able to control at least one visual aspect of at least one of the first and second rendering modules 102, 104 selected from contrast/brightness level and rendering method including at least one of maximum intensity projection, volume rendering, and pre-integrated volume presentation. The user may control rendering settings of the first and second rendering modules 102, 104 through a user interface module 108 as described below.

The first and second rendering modules 102, 104 are configured for constructing the combined volume presentation through the display generation module 40 by making use of a framebuffer (not shown). The combined volume presentation has a high detail region constituting a projection rendered by the second rendering module 104 at higher resolution and a low detail region constituting a projection rendered by the first rendering module 102 at lower resolution. The higher detail and lower detail projections are demarcated based on at least one virtual injection point as described in further detail in the following.

In one embodiment, dual phase imaging data is utilized. That is, an arterial phase of imaging data is acquired for the region of interest by the imaging machine 36 at an early phase after contrast injection and a delayed (parenchymal enhancement) phase of imaging data is acquired for the region of interest at a delayed phase of the region of interest. The early and delayed phases of volumetric data are acquired by time spaced scanning operations by the imaging machine 36, with the delayed scan executed at least 5 or 10 seconds after completion of the early phase scan. In such an embodiment, the first rendering module 102 is configured to render the early phase imaging data, i.e. the arterial phase imaging data. Further, the image processing system 10 comprises a dual phase registration module 120 that is configured to register (warp) the delayed phase volume of imaging data to the arterial phase volume of imaging data in order to compensate for patient/organ motion (e.g. as a result of breathing). The image processing system 10 also comprises a volume enhancement module 122 that is configured to perform parenchymal enhancement of the early phase volume of imaging data with the delayed phase volume of imaging data as registered by the dual phase registration module 120 to produce an enhanced volume of imaging data. That is, the arterial phase volume will be extended or enhanced with delayed phase soft-tissue (tumor blush) enhancement features from the delayed phase volume. The second rendering module 104 is configured to render the enhanced volume of imaging data.

However, a less complex embodiment is envisaged by which the first and second rendering modules 102, 104 operate on the same volume of imaging data. In such an embodiment, the dual phase registration and volume enhancement modules 120, 122 need not be provided.

The image processing system 10 comprises a dual rendering combination module 124. The dual rendering combination module 124 is configured to control an order of rendering of volumes of imaging data by the first and second rendering modules 102, 104. In particular, dual rendering combination module 124 is configured to determine overlapping areas (pixels) rendered by the first rendering module 102 and the second rendering module 104. The dual rendering combination module is configured to control a rendering order so that the first rendering module 102 renders first, followed by the second rendering module, yet for all overlapping area (pixels), the rendering order is reversed. It has been found that a problem can occur with a conventional rendering order when high and low detail renderings are combined. Volumes are normally rendered and constructed in a back to front (with respect to a viewing direction) order by means of a so called painter's algorithm. In the painter's algorithm, the first rendered volume is blended against a black background. For those voxels of the first volume where parts overlap the second volume, black spots can appear. A solution proposed by the present disclosure is to mark these problem voxels in a two dimensional stencil buffer and reverse the rendering order for those overlapping positions. Stencil logic operations are available in graphics libraries like Direct3D or OpenGL.

In more detail, the following steps can be implemented by stenciling control within the dual rendering combination module 124 in order to reverse the rendering order where necessary. Let V10 be a volume of imaging data rendered by the first rendering module 102 and V12 be a volume of imaging data rendered by the second rendering module 104. First, render V10, then setup stencil control whilst rendering V12 in order to determine overlapping pixels based on buffer depth. Using a stencil indicating overlapping pixels, the rendering order is reversed where there is an overlap by first rendering V12 and then rendering V10.

The image processing system 10 comprises a user interface module 108 that allows for a variety of user controls and selections. The user interface module 108 receives user inputs from an input unit (not shown) such as a touchscreen device, which can include the display unit 24, a mouse, a keyboard, video captured gesture controls and the like. An example user input can be selection of at least one virtual injection point, which is used by the image processing system 10 to determine a region to be rendered by the second rendering module 104 and a region to be rendered by the first rendering module 102. The selection of the at least one virtual injection point may be made by positioning a cursor in a displayed volume presentation of the region of interest, in particular by selecting a point in a feeder vessel. Alternatively, the virtual injection points may be processor selected, i.e. automatically selected, such as through the automatic virtual injection point determination module 118 described in greater detail below. The user interface module 108 may also allow user selection of at least one target lesion, such by marking an area in a succession of two dimensional slices of imaging data presented on the display unit 24.

The image processing system 10 comprises an injection simulation module 110. The injection simulation module 110 is configured to simulate an injection from the at least one virtual injection point and particularly the perfusion of injection material from the at least one virtual injection point. Based on the simulated injection, a downstream region from the at least one virtual injection point can be modelled. The downstream region is used to demarcate a region to be rendered at the higher level of detail and a region to be rendered at the lower detail level.

In an embodiment, the injection simulation module 110 is configured to implement a virtual parenchymal perfusion (VP) algorithm to approximate distal vascular territories in a tissue, e.g. liver, region of interest, given the at least one prospective virtual injection point, which uses the imaging data received by the data receiving module 100 as predictive data. In particular, the imaging data used by the simulation algorithm is derived from a three dimensional arterial cone beam computed tomography (CBCT) scan. In one embodiment, the simulation module 110 extracts vascular territories from a vessel-driven geodesic distance map computed from the virtual injection points (positions), which may be user selected. The geodesic potential map results in distance values for each voxel as calculated by the virtual perfusion algorithm. The virtual perfusion algorithm includes a potential term to bias to low distances for contrast injected, i.e. hyper intense, voxels and also tends to lower distance values for voxels closer, in terms of geodesics, to a reference point. Although a vessel driven, geodesic potential algorithm is described in detail herein, other injection simulation algorithms can be used to extract at least one territory or region distal (downstream) to at least one virtual injection point from which a division between the high detail portion and low detail portion of the combined volume presentation can be determined.

The algorithm, which computes the geodesic distance map, encodes the connections between a reference location and the closest blood vessels. The reference location is usually taken as a location on the catheter, e.g. the distal end of the catheter, as determined by the tracking system 35. The reference location that is used may be somewhere on the catheter of the TACE device 16 during contrast acquisition. The exact catheter tip location is not important, as long as it is on the catheter, which is prominently visible in the contrast acquisition volume. Accordingly, description of the reference location as the distal end of the catheter is merely an exemplary embodiment. The reference location may, in an alternative embodiment, be user selected through the user interface module 108. A vascular territory corresponds to the area distal to a prospective injection point, in the sense of the geodesic metric defined by the geodesic distance map. Such a simulation approach is processing efficient as compared to an explicit vessel segmentation algorithm.

In one embodiment, the simulation module 110 is configured to determine a reference catheter point, r, usually corresponding to the distal end of the catheter as determinable from contrast imaging data. The simulation module 110 is configured to compute a geodesic distance map using imaging data and the reference location at the distal end of the catheter. The simulation module 110 is configured to extract at least one vascular territory using the geodesic distance map and at least one virtual injection point. The steps of determining the reference location r, computing the geodesic distance map and extracting the vascular territories are described further below. The processing module 106 is configured to control the second rendering module 104 and the first rendering module 102 to render the dual detail level volume presentation based on the extracted at least one vascular territory.

Point r serves as a reference location, i.e. the most proximal injection point, considered in subsequent computations.

The vascular-driven geodesic distance map is computed to encode distances from the catheter point r to any location in the imaging data, following blood vessels. Points along or close to the vessels are given low geodesic distance values, while areas outside the vessels result in large geodesic distances. Such a geodesic formulation can be seen as a crude approximation to a fluid simulation.

The geodesic distance $D_r(x)$ from r to any location x is computed following a minimal path approach [6]:

$$D_r(x) = \inf_{C \in C_{r \to \infty}} \int_\Omega P(C(s)) ds \qquad (1)$$

where C(s) is a curve of arc-length s in the set of all possible curves $C_{r \to x}$ from r to x, and P(.) is the potential term. The geodesic distance is thus obtained as the minimal cumulative potential connecting r to x.

The potential is designed to favor hyper-intense areas of the imaging data such as contrast injected vessels. An exemplary potential function is:

$$P(x) = \left\{ 1 - \frac{\tilde{I}(x)}{1 + \|\tilde{I}(x)\|} \right\}^3 \qquad (2)$$

which corresponds to a sigmoid-shaped function applied to the heuristically normalized image intensity $$\tilde{I}(x) = \frac{I(x) - M}{D}.$$

Mean M and deviation D can be empirically set to scale the sigmoid as a soft threshold around the typical pseudo-Hounsfield values of contrasted parenchyma, so that hyper-intense contrast injected vessels obtain positive values.

In order to extract the vascular territory, the geodesic map is used, which encodes the vascular-driven connectivity within the three dimensional imaging data. For any location x, a minimal geodesic path can be traced back to the catheter point, r. Similarly, it is possible to define the vascular territory T(i) distal to a virtual injection point i, which may be user provided:

$$T(i) = \{x | D_r(x) \geq D_r(i), i \in C_{r \to \infty}^* \} \qquad (3)$$

where $C_{r \to x}^*$ is the minimal path from the catheter r to x. This computation can be performed from more than one virtual injection point i to defined a composite vascular territory.

Given the precomputed geodesic map, the extraction of any vascular territory can be performed efficiently, thereby allowing rapid interactive exploration of prospective injection points.

The simulation module 110 is configured to output a mapping volume with labels describing which of the voxels of the imaging data will be reached by the proposed at least one virtual injection and which subset of these voxels will contain enhanced contrast information. The labelled subset of voxels with enhanced contrast intensity values allows for the combined volume presentation to highlight the vascular structure carrying injection material from the at least one virtual injection point to a lesion. The overall area of virtual perfusion impregnation in the parenchyma can be utilized to determine that part of the combined presentation that is rendered by the second rendering module 104. That is, the processing module 106 is configured so that an extracted virtually injected territory as determined by the injection simulation module 110 is rendered by the second rendering module 104. In one embodiment, the second rendering module 104 renders an extended volume, which contains the arterial phase volume imaging data plus second phase features like tumor blush from the delayed phase volume imaging data.

The image processing system 10 comprises a segmentation module 112 that is configured to segment the three dimensional volume of imaging data, e.g. an arterial phase volume, based on trained object models into bone (ribcage) voxels and possibly also organ (liver, kidney) labels. The output is maintained in a mapping volume where for each voxel a label describing the segmentation type is stored. The segmentation module 112 determines the mapping of segmented voxel labels, which is also able to determine a region of interest. The region of interest may determine boundaries for other processing modules, such as for the dual phase registration module 120 and the volume enhancement module 122.

The image processing system 10 comprises a graphics module 126 that is configured to include graphical highlights in the combined volume presentation described herein. For example, any of the following graphical highlights may be added: a lesion region, a lesion boundary, a catheter reference point (e.g. catheter distal end), at least one virtual injection point, an injection member path from a catheter distal end to a virtual injection point, different injection member paths from a catheter distal end to different virtual injection points, an injected region, injection fluid perfusion from at least one virtual injection point, different highlights for injection perfusion from different injection points, feeder vessels to a lesion, vessels in a neighborhood region to a determined injected region etc. Where plural graphical highlights are included they may be presented in a visually differential way such as by different coloring.

The combined detail volume rendering disclosed herein allows enhanced visibility of the effect(s) of an injection at a candidate injection site in a processing efficient way. Further, the present disclosure provides a number of presentation control features that will be described further below.

The user interface module 108 allows at least one injection point to be inserted and/or manipulated interactively by selecting a location in a vessel in a volume presentation. The volume presentation before virtual injection points are inserted may be constructed at the lower level of detail by the first rendering module 102 to provide a clear, easy to follow presentation of the vessels for a user. Subsequently, an injected volume area from the virtual injection point is computed by the simulation module 110 in addition to vessels within the injected volume area. Based on the injected volume area, a combined presentation will be rendered by sampling (or resampling) the imaging data, with the injected volume area rendered by the second rendering module 104 so as to clearly visualize anatomical features distal of the virtual injection point at the higher level of detail. In the proposed solution, only the vessels and parenchyma area on the injected trajectories are re-sampled and shown in detail.

The image processing system 10 comprises an automatic feeder determination module 114 configured to determine feeder vessels to a lesion based on segmented lesion information associated with the imaging data and catheter location (e.g. distal end) information associated with the imaging data. The lesion information may result from an automated segmentation process through the segmentation module 112 or through user identified lesion information through the user interface module 108. In particular, the user may select boundaries of at least one lesion by in each of a succession of presentations of slices of imaging data. The catheter location information may be based on a user input through user interface module 108 or through automated catheter position information determined based on contrast imaging data. The automatic feeder determination module 114 may implement a path finding algorithm (as known in the art) in order to find all vessel feeders from the lesion to the catheter. In particular, the path finding algorithm may operate determining intersections of candidate feeders with lesions contours. The feeders are identifiable from the contrast enhanced imaging data. Based on the intersections, a connectivity network to the catheter position is calculated and vectorized. The determined feeder vessels may be graphically highlighted in the combined presentation through the graphics module 126.

The image processing system 10 comprises an injection member path determination module 128 configured to determine a path from the catheter distal end to a virtual injection point. Plural paths may be determined for plural virtual injection points. The injection member path determination module 128 uses information on virtual injection point location, which may be user decided through the user interface module 108 or automatically decided through an automated virtual injection point determination module 118 (described below). The injection member path determination module 128 uses a path finding algorithm, e.g. as described above, to determine respective paths from the catheter location to the virtual injection points. The respective paths are graphically indicated in the combined presentation through the graphics module 126 in order to guide a user in positioning the injection member for locating a distal end of the injection member at the location of the virtual injection point.

In an embodiment, the injection member path determination module 128 is configured so that when a virtual injection point is added to the volume presentation, the path from the catheter to the virtual injection point, represented by a centerline, is calculated and graphically shown in the volume presentation through the graphics module 126. To do so, the following injection point logic is implemented. When the added virtual injection point is over the centerline of a previous virtual injection point, the intersection with the three dimensional centerline representation is used as the new injection point position. If no intersection is found and a point on a vessel tree is selected, then the first rendering module 102 is probed by means of a ray casting volume intersection calculation. If no intersection is found, then the second rendering module 104 is tested for intersections.

The image processing system 10 comprises an automatic virtual injection point determination module 124 configured to automatically determine at least one virtual injection point. In particular, a user is able to select, through the user interface module 108, a destination point (usually a destination point within a lesion) in the region of interest in a volume presentation thereof and to select a command to determine at least one virtual injection point. The automatic virtual injection point determination module 124 communicates with the automatic feeder determination module 120 to calculate at least one feeder path from the user selected destination point to the catheter position. The automatic virtual injection point determination module 124 is configured to insert a virtual injection point along each of the at least one feeder path, usually at a preset distance (e.g. 1.5 cm) from the user selected destination point. The preset distance can be user controllable through the user interface module 108. Further, and optionally, the injection simulation module 110 and the processing module 106 are configured to be responsive to the automatically determined virtual injection points to produce a combined presentation at two levels of detail where the higher and lower levels of detail are designated based on the automatically determined at least one virtual injection point. In this way, at least one virtual injection point, a simulation perfusion therefrom and at least one feeder path from a catheter distal end to each virtual injection point can be determined automatically and graphically highlighted in the combined, dual detail level, volume presentation, with relatively low processing requirements, with a single user selection of a destination point.

A further possible feature of the image processing system 10 is shown in FIG. 2 in the form of neighborhood module 130. Neighborhood module 130 is configured to scale (enlarge) the area to be shown in the combined presentation in high detail. In particular, an injected area can be derived from the result of an injection simulation performed by the injection simulation module 110. A neighborhood area can be defined with respect to the injected area. The neighborhood module 130 is configured to process the imaging data to determine all non-injected (as determinable based on output from the simulation module 110) contrasted information, arriving from all possible directions and branches, into the neighborhood area. The vessels in the neighborhood area so determined are presented in the combined presentation at the higher level of detail and may also be presented in a different color from the injected area. The neighborhood area can be (increased/decreased) by a preset scalar value relative to the injected area.

Figure 3:
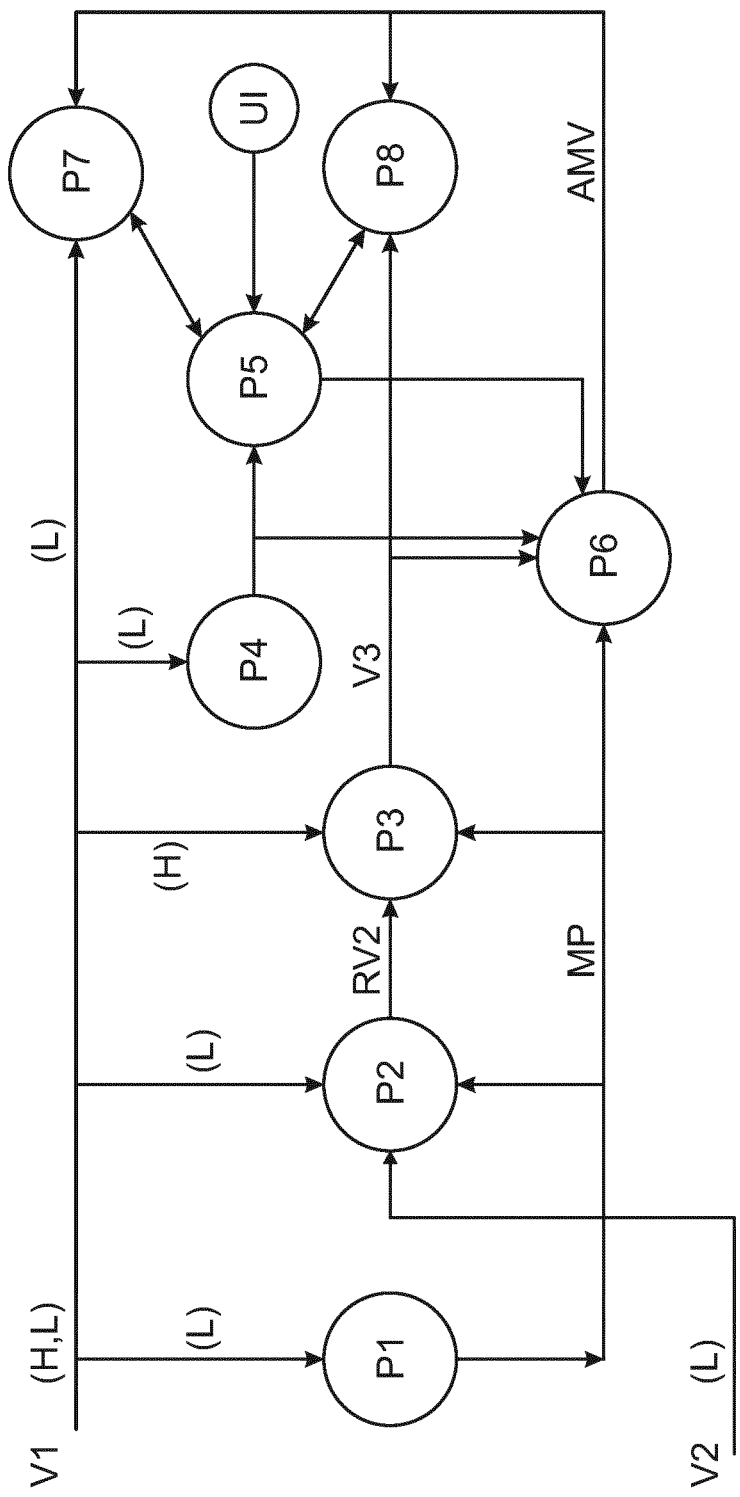
FIG. 3 is a data flow diagram for processing source imaging data to a combined volume presentation according to a first embodiment of the methods disclosed herein.

FIG. 3 shows a data flow diagram illustrating data transformation processes for producing a dual detail level combined presentation as described herein. A number of data processing functions P1 to P8 are illustrated, which will be detailed below and related to the previously described image processing system. FIG. 3 provides a first embodiment of the methods described herein.

Figure 4:
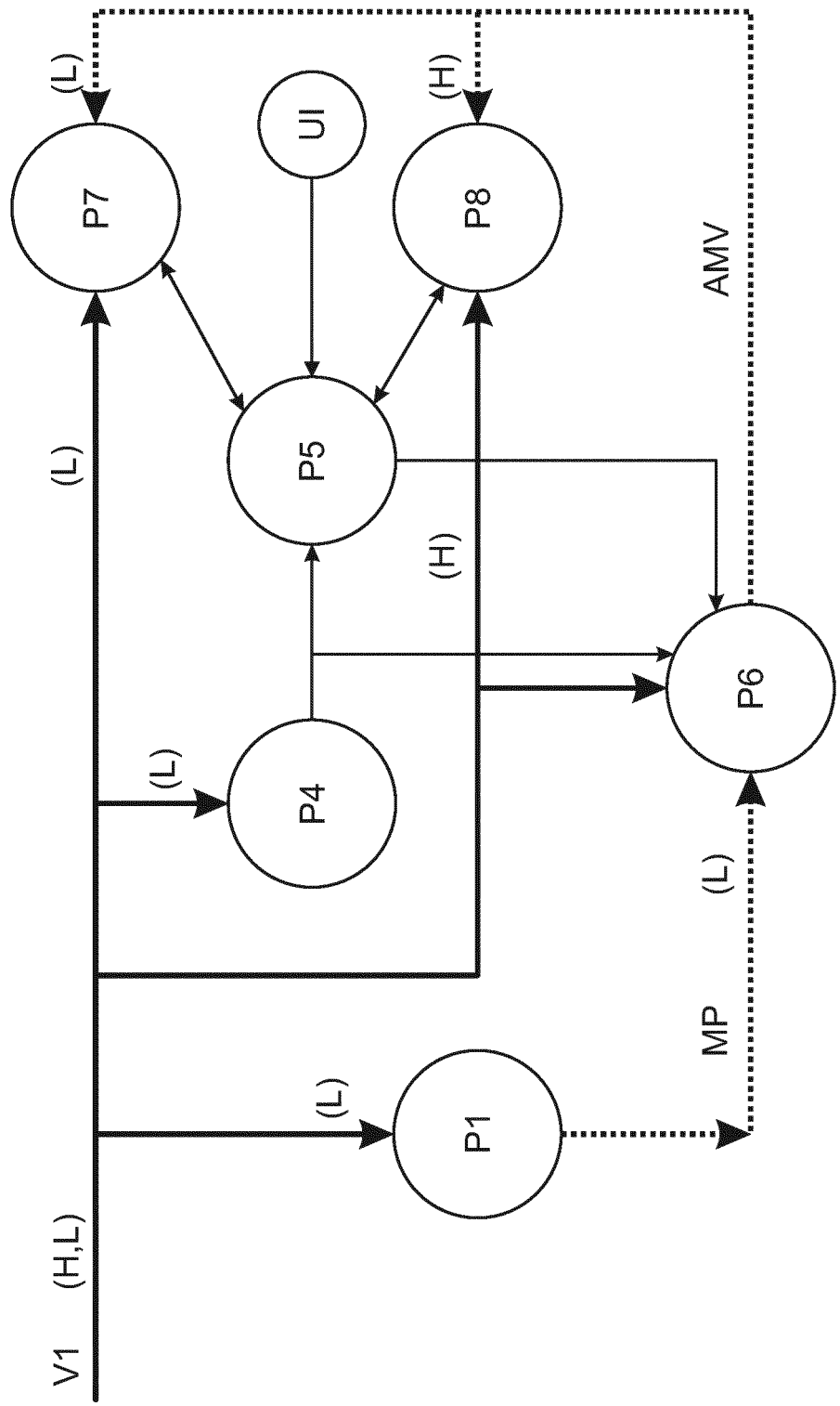
FIG. 4 is a data flow diagram according to a modified embodiment of the methods disclosed herein to that of FIG. 3.

In the example of FIG. 3, a first volume of imaging data V1 is received corresponding to an arterial phase after contrast agent injection. A second volume of imaging data V2 is also received corresponding to a delayed phase after the arterial phase. The use of arterial and delayed phase imaging data is preferred, but not necessary as shown by the embodiment of FIG. 4 (described further below) which does not make use of dual phase imaging data. The imaging data is received through the data receiving module 100. The first volume of imaging data V1 can be received in two forms: at high detail (i.e. higher spatial resolution) H and at low detail L (i.e. lower spatial resolution). To receive the first volume of imaging data V1 at the two detail levels, a sampling process can be used that samples the original imaging data at different resolution levels.

In data process P7, a first volume rendering is executed at a relatively low level of detail by rendering the low detail, arterial phase volume of imaging data. The process of P7 is carried out through the first rendering module 102. The rendered data is output to a presentation control process P5 described further below.

In data process P1, the arterial phase volume V1 will be segmented based on trained object models into bony (ribcage) and organ (liver, kidney) information. Data process P1 outputs a mapping volume MP, where, for each voxel of the imaging data, a label describing the segmentation type (organ, bone) is stored. The mapping volume MP will also define a region of interest for the data processes P2, P3 and P6 described below.

In data process P2, the delayed phase volume V2, at the low level of detail or resolution L, will be registered (warped) to the arterial phase volume V1 at the low level of detail L in order to compensate for patient/organ motion. Such registration processes are known in the art. For example, a known non-rigid deformation and registration process may be utilized. Data process P2 produces a registered volume of delayed phase imaging data RV2. The registration process of P2 can be executed through the dual phase registration module 120.

In data process P3, the arterial phase volume of imaging data V1 at the high level of detail H will be extended with delayed phase soft-tissue (tumor blush) enhancement features from the registered volume of delayed phase imaging data RV2. The data process P3 produces an enhanced volume of imaging data V3 that combines the arterial phase imaging data V1 and the delayed phase imaging data V2. The data enhancement process P3 can be performed through the volume enhancement module 122.

In data process P8, the enhanced volume of imaging data V3 is rendered through the second rendering module 104. The rendered data is provided to the presentation control process P5.

In data process P4, a reference part of the catheter will be (manually or automatically) determined in the arterial phase volume V1. The reference part can be entered through the user interface module 108, but is usually automatically determined near the distal end of the catheter based on image analysis. Accordingly, the processes described herein are usually carried out during an interventional procedure when the medical device 16, and particularly the catheter thereof, is in situ, although the methods claimed are concerned with imaging processes and do not extend to catheter placement. The catheter tip position is output from data process P4 to be utilized in data processes P5 and P6.

Data process P6 performs an injection simulation based on the region of interest received from data process P2, the catheter distal end position as a reference point r (as described above) received from data process P4 and the enhanced volume of imaging data V3 received from data process P3. Further, the data process P6 makes use of at least one virtual injection location, which has been obtained through data process P5 described below. The injection simulation can be carried out through the injection simulation module 110. In data process P6, an injected area is simulated as though an injection were made through each of the at least one virtual injection point using the enhanced volume of imaging data V3. In one embodiment, the injection simulation process P6 is based on a notion of geodesic potential field mapping as has been described above with respect to the injection simulation module 110. Data process P6 outputs an annotated mapping volume AMV with labels describing which voxels of the volume V3 will be reached by the proposed at least one virtual injection and which subset of these voxels will contain contrast information (i.e. which of these voxels correspond to blood vessels). The annotated mapping volume AMV is received by the first and second rendering processes P7 and P8. At least one extracted territory or area labelled by the AMV as being reached by the simulated virtual injection is rendered at the higher level of detail by rendering process P8 and at least one area labelled by the AMV as not being reached by the simulated virtual injection is rendered by the lower detail rendering process P7. In some embodiments, the injection simulation may extract a territory reached by the at least one virtual injection and all voxels within that territory may be labelled in the annotated mapping volume AMV as being reached by the virtual injection to ensure a coherent rendering of a continuous area at the higher level of detail.

In rendering processes P7 and P8, based on the information in the annotated mapping volume AMV, the corresponding volume areas are re-sampled and visualized by a designated rendering module 102, 104. The two separate rendering processes P7 and P8, executed through separate renderers or rendering modules 102, 104, each have their own spatial resolution, and optionally also at least one of their own rendering method, contrast/brightness transfer function, color scheme, white space speed optimization, etc. where these features can be user controlled. A combined volume presentation can be constructed through suitable control through the presentation control process P5 in a framebuffer (not shown).

In presentation control process P5, executed through the processing module 106, a number of viewing control tasks will be executed. A user input UI can be received through the user interface module 108 to control visualization setting of the rendering processes P7 and P8 (e.g. visual transfer function settings). Further, control of which areas of the combined presentation are rendered through rendering process P7 and which are rendered through the rendering process P8 is executed by presentation control process by making use of the annotated mapping volume AMV as described above. Further, volume ordering control as has been described above with respect to the dual rendering combination module 124 is performed by data process P5 and the first and second rendering processes P7 and P8 are controlled and the rendered data combined accordingly. Additionally, the inclusion of graphical annotations like the catheter distal end (and perhaps also the elongate catheter itself), virtual injection points, injection member paths, feeder paths, etc. Furthermore, the determination of feeder vessels, determination of injection member paths, and automatic virtual injection points as has been described above with respect to the automatic feeder determination module 114, the injection member path determination module 128 and the automatic virtual injection point determination module 118 is controlled by data process P5.

FIG. 4 illustrates a data flow diagram for an alternative embodiment that does not make use of dual phase imaging data. FIG. 4 provides a second embodiment of the methods described herein. In this case the registration process P2 and the volume enhancement process P4 of FIG. 3 can be omitted. Instead, a single volume of imaging data V1 can be obtained, which is sent to the low detail rendering process P7 at a low detail level for the imaging data and which is sent to the high detail rendering process P8 at a high detail level. Based on at least one virtual injection point obtained through presentation control process P5, an injection simulation is run through process P6 to produce an annotated mapping volume AMV designating at least one injected area that will be reached by an injection performed at the at least one virtual injection point to be rendered by the high detail rendering process P8. Further, graphical annotations will be included by the presentation control process P5 so as to mark in the dual detail, combined presentation at least one virtual injection point, the injected area as determined by the injection simulation of process P6, an injection member path from a catheter distal end to the at least one virtual injection point and a catheter distal end.

Figure 5:
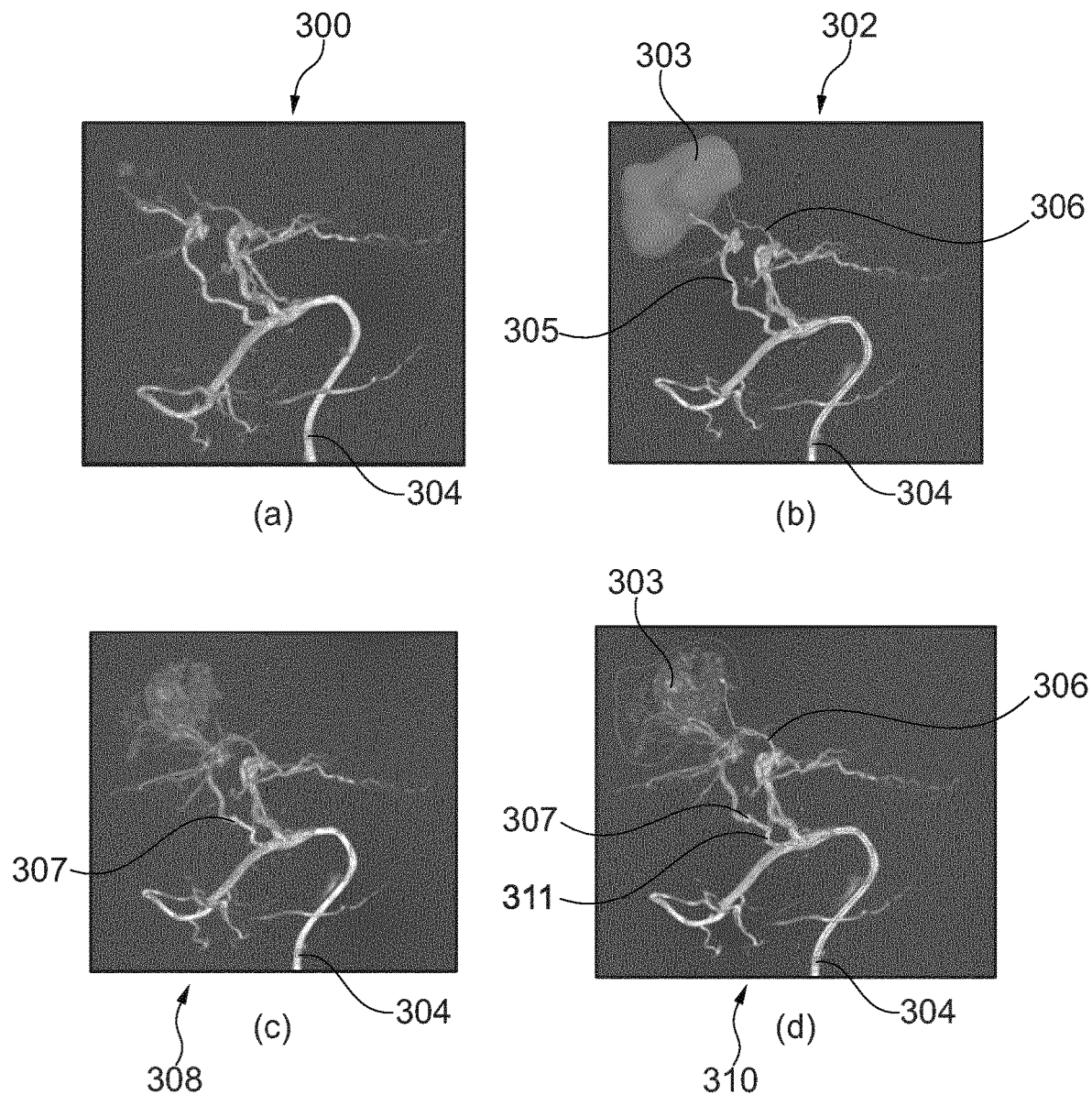
FIG. 5 is a series of volume presentations according to the present disclosure.
Figure 6:
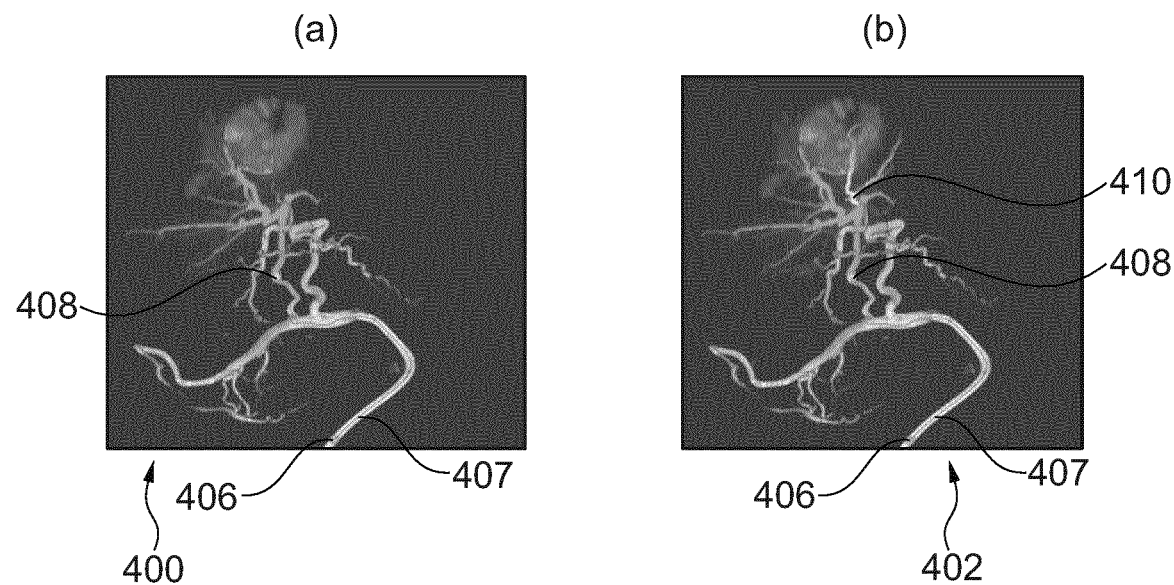
FIG. 6 illustrates further volume presentations according to the present disclosure.

Having described aspects of the image processing system 10 and the data processes with respect to FIGS. 1 to 4, operative interactions and volume presentations are described with respect to FIGS. 5 and 6.

FIG. 5 shows a sequence of volume presentations 300, 302, 308, 310 produced by the image processing system 10 of the present disclosure.

FIG. 5(a) shows an initial volume presentation 300 acting as a starting presentation for user interaction and virtual injection point selection. The volume presentation 300 of FIG. 5(a) is rendered in process P7 by the first rendering module 102 based on the volume of imaging data V1 after removal of bone based on segmentation process P1 through segmentation module 112. Accordingly, the volume presentation 300 of FIG. 5(a) is rendered at a relatively low detail level, which allows for a clear volume presentation of the main vessel structures. Where dual phase imaging data is obtained, the volume presentation 300 is of the arterial phase. Further graphically highlighted in the volume presentation is a catheter reference point 304 (as a colored dot in one example) that has been automatically determined in process P4 through image analysis of fluoroscopic imaging data. As such, the imaging data has been obtained with the catheter in situ and the volume presentation 300 is useful for planning an embolization injection from an injection member extendable from the catheter.

In FIG. 5(b), a volume presentation 302 is shown in which a lesion 303 has been graphically highlighted (as a colored portion with a clear outer boundary in one example) through the graphics module 126. The lesion has been identified through user marking of outer bounds thereof in a presentation of two dimensional, orthogonal slices of the imaging data V1. The volume presentation 302 further shows graphics illustrating results of automatic feeder determination through the automatic feeder determination module 114. In particular, different colored lines 305, 306 are included to illustrate paths from the catheter reference point 304 to the lesion 303 that includes all available feeder vessels. The volume presentation 302 is produced by the first rendering module 102 at the lower level of detail. Like FIG. 5(a), the volume presentation 302 does not yet include dual detail levels as a virtual injection point has not yet been selected.

In FIG. 5(c), a volume presentation 308 is shown that has combined detail levels according to various embodiments of the present disclosure. One virtual injection point 307 is selected in one of the feeder vessels illustrated by line 305 in FIG. 5(b). The injection point 307 is user selected in the presentation 302 of FIG. 5(b) through the user interface module 108. An injection simulation from the virtual injection point 307 is run, through the injection simulation module 110, in process P6 based on imaging data and the position 304 of the catheter distal end, which results in an annotated three dimensional data mapping AMV noting which voxels are simulated to be reached by material injected at the virtual injection point 307. Based on the annotated mapping AMV, particularly an injected area derived therefrom, the volume presentation 308 includes a high detail injected area distal to the virtual injection point 307 rendered by the second rendering module 104 in process P8 and a low detail, non-injected area proximal to the virtual injection point 307 rendered by the first rendering module 102 in process P7. The low and high detail areas of the combined presentation 308 are seamlessly integrated with one another in the presentation. Where dual phase imaging data is utilized, the high detail area presents enhanced volume of imaging data V3 in which the arterial phase volume V1 has been enhanced by features from the delayed phase volume V2. Further, the injected area is graphically highlighted by coloring the injected area with shading based on those voxels that are deemed to be reached by the injection based on the simulation.

By way of the automated feeder detection shown in FIG. 5(*b*), it is possible to reveal that the injection plan of FIG. 5(*c*) encompasses an injection in only one of the two detected feeder vessels. Consequently, an operative can plan a further injection point. The automatically detected feeder vessels can be shown before or after a virtual injection point has been selected to readily reveal any insufficiencies in an injection plan.

In FIG. 5(*d*), a combined volume presentation 310 is illustrated which also has high and low detail areas. Here, a user has selected a first virtual injection point 307. Further, the second feeder vessel is graphically highlighted at 306 to allow an operative to realize that one of the feeders has been missed. Consequently, a second virtual injection point can be placed in the second feeder vessel 306 through the user interface module 108. The injection simulation process can re-run so that an injection simulation from both the first virtual injection point 307 and the new, second virtual injection can be performed to determine a revised annotated mapping AMV of the volume(s) of imaging data. The further combined volume presentation can be produced that includes an expanded injected area based on the additional, second virtual injection point as compared to FIG. 5(*d*), which is rendered at the higher level of detail and which includes graphical highlighting (e.g. color shading) to show the injected area reached by the injections from the virtual injection points according to the simulation. The new combined volume presentation can show additional graphical features. Injection member paths 311 from the catheter distal end 304 to the virtual injection points 307 are shown by different colored lines for injection member guidance purposes. Further, an outer contour of the lesion 303 can be graphically highlighted to allow extent of coverage by the proposed injections to be visualized. The combined presentations 308, 310 of FIGS. 5(*c*) and 5(*d*) allow the injected vessels, including feeding vessels and the connected lesion area(s), to be visualized by means of a volume render solution that is optimized for higher detailed, lower contrast information. In order to visualize, at high detail, vessels and connecting areas between vessels, a mapping output from the injection simulation can be processed to derive a coherent vascular territory that includes the whole of the injected area, which is then displayed at the high detail level. Accordingly, the injected vessels and parenchyma area on the injected trajectories are shown in high detail, with the remainder of the presentation shown in lower detail to ensure clear visualization and efficient processing.

By moving virtual injection points from proximal positions to more distal positions, and in the reverse direction, the effect on the injected vessels and resulting tumor and feeding vessel embolization can be evaluated on the fly to plan optimal injection positions that suitably balances lesion coverage and selectivity. Additionally, the injection result including the total affected area and the injected vessels can be shown in the combined volume presentation and in accompanying orthogonal slices if desired.

If not carefully checked, sometimes important feeders, coming from unexpected more proximal branches, can be missed. In FIGS. 5(*a*) and 5(*b*), combined presentations 400, 402 that illustrate presentation enhancement by showing not only the injected area in higher detail, but also a neighborhood area as determined by the neighborhood module 130. In FIG. 6(*a*), the presentation 400 shows an injected area distal to a virtual injection point 408 at a higher level of detail and colored for ease of visualization than an area proximal to the virtual injection point 408. Further, graphics are included to highlight the injection member path 407 from a catheter distal end 406 to the virtual injection point. The catheter distal end 406 and the virtual injection point 408 are also graphically illustrated through the graphics module 126. The injected area is determined based on output from an injection simulation process P6 (which usually results in a simulated injected three dimensional volume) based on an assumed injection from the injection point 408. When activated, the neighborhood area module 130 is configured to determine a neighborhood area or volume (such as through a scalar area or volume expansion of the injected area or volume) based on the injected area or volume and to determine all feeders and vessels from the contrast enhanced imaging data in the neighborhood area or volume. The feeders and vessels in the neighborhood area can be determined using path finding processing on the contrast enhanced imaging data. The feeders and vessels in the neighborhood area can be graphically highlighted, such as by a different color from the graphical highlighting in the injected area. The neighborhood area may also be presented at the higher level of detail. FIG. 6(*b*) thus shows additionally graphically highlighted vessels 410 in the neighborhood of the injected area based on neighborhood vessel determination executed by the neighborhood module 130. This feature aids in an operative avoiding missing relevant vessels for a successful embolization procedure.

Figure 7:
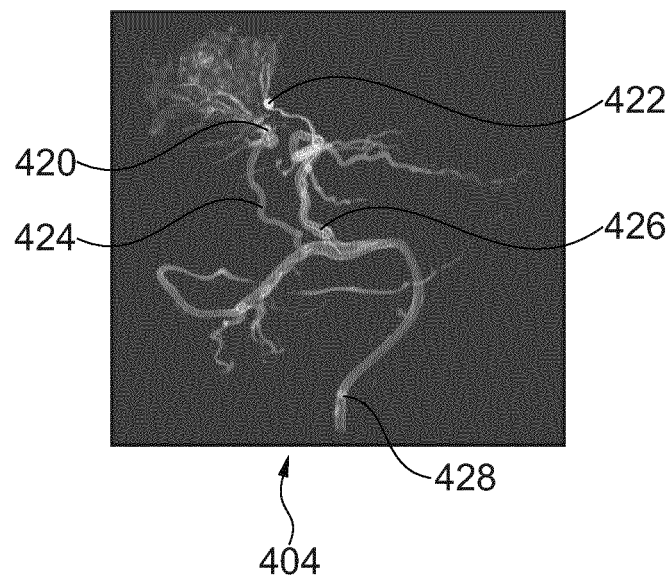
FIG. 7 illustrates another volume presentation according to the present disclosure.

In FIG. 7, a combined presentation 404 is shown having graphically illustrated first and second virtual injection points 420, 422 that are user selected through the user interface module 108. Further, a catheter distal end 428 is graphically illustrated, where the catheter distal end 428 is determined from image analysis (for example). Injection member paths 424, 426 have been determined using path logic processing of the imaging data through the injection member path determination module 128, and extend from the catheter distal end 428 to respective virtual injection points 420, 422. An injected area, downstream of the virtual injection points 420, 422, is graphically highlighted and rendered in relatively high detail. The injected area is derived from an injection simulation performed through the injection simulation module 110. In this case, the injected area is rendered using a different volume rendering preference than in FIGS. 5 and 6. Whilst the second rendering module 104 is still operating at higher detail than the first rendering module 102, the transfer function (such as the spatial resolution and/or contrast settings) have been adapted to allow the vessels in the injected area to be yet more clearly visualized. Such adaptation of the visualization setting of the first rendering module may be user selectable through the user interface module 108.

In one possibility, the combined volume presentation 404 of FIG. 7 may be automatically determined simply by clicking on or otherwise selecting a destination point in a visible tumor. That is, usually the core of the (highly vascular) tumor region is partially visible in an initial presentation (such as that shown in FIG. 5(a)), but the access trajectory is usually difficult to figure out. From such a presentation, a destination point can be selected by a user. Alternatively, the destination point can be indicated in an orthogonal slice presentation. Given the selected destination point or location, the access paths (feeders) to the selected destination point in the tumor to the catheter distal end is calculated through the automatic feeder determination module 114. A virtual injection point can be placed along each feeder at a controllable (preset) distance (e.g. 1.5 cm) from the destination point through the automatic virtual injection point determination module 118. An injection simulation can be automatically performed for the virtual injection points. As a result, by a single selection of a destination target on the tumor core in FIG. 5(a), the graphical and visualization enhancements shown in FIG. 7 can be obtained. In particular, the injected area is visualized at higher detail and colored/otherwise graphically highlighted to show the simulated injection, virtual injection points 420, 422 can be determined and graphically inserted and injection member paths 424, 426 can be determined and graphically inserted.

In another exemplary embodiment of the present invention, a computer program or a computer program element is provided that is characterized by being adapted to execute the method steps of the method according to one of the preceding embodiments, on an appropriate processing system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system for planning a location of at least one injection point for a medical procedure, the image processing system comprising:
   a data receiving module configured to receive at least one volume of imaging data for a region of interest;
   first and second rendering modules configured to render the at least one volume of imaging data;
   a processing module configured to obtain at least one virtual injection point indicating a location in a network of blood vessels for an injection;
   wherein the second rendering module renders imaging data at a higher level of detail than the first rendering module;
   wherein the processing module is configured to control the first and second rendering modules to construct a combined volume presentation including a first volume region rendered by the first rendering module and a second volume region based on imaging data at the higher level of detail rendered by the second rendering module, and
   wherein the processing module is configured to designate the first and second volume regions based on the at least one virtual injection point.

2. The image processing system of claim 1, comprising a user interface module configured to receive a user selection of the at least one virtual injection point; and/or
wherein the second volume region is located in the combined volume presentation downstream of the at least one virtual injection point relative to a direction of blood flow in the network of blood vessels.

3. The image processing system of claim 1, wherein the data receiving module is configured to receive dual phase computed tomography imaging data including arterial phase imaging data and delayed phase imaging data, wherein the processing module is configured to register the arterial phase imaging and the delayed phase imaging data and wherein the first rendering module is configured to render the arterial phase imaging data and the second rendering module is configured to render the registered arterial phase imaging data and delayed phase imaging data.

4. The image processing system of claim 1, wherein the first and second rendering modules are configured to operate on the same volume of imaging data, yet to render the imaging data at different levels of detail and/or
wherein the second rendering module renders at a higher spatial resolution than the first rendering module; and/or
wherein a rendering selection module is provided that is configured to allow a user to select at least one visual aspect of at least one of the first and second rendering modules.

5. The image processing system of claim 1, wherein the processing module is configured to obtain at least one adapted virtual injection point based on a received command to add at least one virtual injection point, delete at least one virtual injection point, or to move at least one virtual injection point, and wherein the processing module is configured to control the first and second rendering modules to construct an adapted combined volume presentation including first and second volume regions, respectively rendered by the first and second rendering modules, designated based on the at least one adapted virtual injection point.

6. The image processing system of claim 1, comprising an injection simulation module configured to simulate an injected region from each at least one virtual injection point, wherein the processing module is configured to designate the first and second volume regions based on the injected region; and
wherein the simulation module is configured to simulate the injected region from each at least one virtual injection point by processing the at least one volume of imaging data using a virtual perfusion algorithm that estimates injection material perfusion from each at least one virtual injection point.

7. The image processing system of claim 6, wherein the processing module is configured to construct the combined volume presentation including a highlighted volume region that has been graphically highlighted to indicate tissue reached by an injection from each at least one virtual injection point based on the simulation.

8. The image processing system of claim 6, wherein the processing module is configured to determine an injected region based on the at least one virtual injection point and to determine all non-injected vessels in a neighborhood region to the injected region, and wherein the processing module is configured to control the first and second rendering modules to construct the combined volume presentation so that the second volume region includes the injected region and the non-injected region.

9. The image processing system of claim 6, comprising:
i) a segmentation module configured to segment a lesion from the imaging data, and wherein the processing module is configured to graphically highlight the lesion in the combined volume presentation; and/or
ii) an automatic feeder determination module configured to determine at least one feeder vessel to a lesion, wherein the processing module is configured to graphically highlight a feeder path along the at least one determined feeder vessel to the lesion.

10. The image processing system of claim 1, comprising:
an automatic injection member path determination module configured to obtain a location of a distal end of a catheter that feeds an injection device, and to automatically determine an injection member path from the location of the catheter distal end to the virtual injection point through the network of blood vessels, wherein the processing module is configured to graphically highlight the injection member path in the combined volume presentation; and/or
an automatic virtual injection point determination module configured to automatically determine the at least one virtual injection point based on a location of a lesion obtained from the at least one volume of imaging data and a path to the lesion, and wherein the processing module is configured to designate first and second volume regions based on the automatically determined at least one virtual injection point.

11. An imaging system, comprising:
the image processing system of claim 10; and
an imaging machine for obtaining tomographic imaging data corresponding to the at least one volume of imaging data.

12. A medical system comprising:
a transarterial catheter embolization device configured to navigate bodily vessels and deliver treatment material including embolization material at the site of a lesion; and
the imaging system of claim 11.

13. A medical system comprising:
a transarterial catheter embolization device configured to navigate bodily vessels and deliver treatment material including embolization material at the site of a lesion; and
the image processing system of claim 1.

14. A method for planning a location of at least one injection point for a transarterial embolization procedure, the method comprising:
obtaining at least one virtual injection point indicating a location in a network of blood vessels for an injection of treatment material including embolization material; and
controlling first and second rendering modules to construct a combined volume presentation including a first volume region rendered by the first rendering module and a second volume region rendered by the second rendering module;
wherein the second volume region is rendered at a higher level of detail than the first volume region; and
wherein the first and second volume regions are designated based on the at least one virtual injection point.

15. A non-transitory computer-readable storage medium having stored thereon a computer program having instructions which, when executed by at least one processor, cause the at least one processor to perform the method steps of claim 14.

* * * * *